US005654142A

United States Patent [19]
Kievits et al.

[11] Patent Number: 5,654,142
[45] Date of Patent: Aug. 5, 1997

[54] METHOD FOR NUCLEIC ACID AMPLIFICATION USING INOSINE TRIPHOSPHATES TO PARTIALLY REPLACE GUANOSINE TRIPHOSPHATES IN THE SYNTHESIS OF MULTIPLE RNA COPIES

[75] Inventors: Tim Kievits, Vught; Peter Franklin Lens, Den Bosch; Henriette Maria Aleida Adriaanse, Boxmeer, all of Netherlands

[73] Assignee: Akzo Nobel N.V., Arnhem, Netherlands

[21] Appl. No.: 403,540

[22] Filed: Mar. 14, 1995

Related U.S. Application Data

[63] Continuation of Ser. No. 110,919, Aug. 24, 1993, abandoned.

[30] Foreign Application Priority Data

Aug. 24, 1992 [EP] European Pat. Off. .............. 92202564

[51] Int. Cl.⁶ ............................. C12Q 1/68; C12P 19/34
[52] U.S. Cl. .......................... 435/6; 435/91.2; 435/91.21; 935/77; 935/78
[58] Field of Search .......................... 435/6, 91.21, 81.2; 935/77, 78

[56] References Cited

U.S. PATENT DOCUMENTS

| 5,091,310 | 2/1992 | Innis | 435/91 |
| 5,142,033 | 8/1992 | Innis | 536/27 |

FOREIGN PATENT DOCUMENTS

| 0329822 | 8/1989 | European Pat. Off. . |
| WOA9003443 | 4/1990 | WIPO . |

OTHER PUBLICATIONS

D.R. Mills et al., "Structure independent nucleotide sequence analysis," Proceedings of the National Academy of Sciences of USA, vol. 76, No. 5, pp. 2232–2235, May 1979, Washington D.C.

G.C. Huang et al., "Molecular cloning of a human thyrotropin receptor cDNA fragment," FEBS Letters, vol. 264, No. 2, pp. 193–197, May 1990, Amsterdam NL.

F. Seela and A. Roeling, "Deazapurine Containing DNA Efficiency of C-7G-DTP C-7A-DTP and C-7I-DTP Incorporation during PCR-Amplification and Protection from Endodeoxyribonuclease Hydrolysis," Nucleic Acid Res 20(1) pp. 55–61, 1992.

M.A. Innis et al., "DNA Sequencing with Thermus aqauaticus DNA polymerase and direct sequencing of PCR amplified DNA," Proceedings of the National Academy of Sciences of USA, vol., 85, pp. 9436–9440, Dec. 1988, Washington USA.

Sooknanan et al. (1994) Biotechniques 17(C): 1077–1080, 1083 1985.

Gingeras, T.R. et al. A Transcription—Based Amplification System (1990) in PCR Protocols: A Guide to Methods and Applications; Academic Press, Inc., pp. 245–252.

Promega Corporation, Promega Protocols and Applications Guide, 2nd Ed. (Mar., 1991) pp. 88–89.

Perkin Elmer Cetus Biotechnology Catalog (1991) p. 54.

Innis et al. "Optimization of PCRs." PCR Protocols: A Guide to Methods and Applications. pp. 3–12 (1990).

*Primary Examiner*—Lisa B. Arthur
*Attorney, Agent, or Firm*—William M. Blackstone; Mary E. Gormley

[57] ABSTRACT

The invention is an improved method for the amplification of nucleic acid, wherein ribonucleotides that weaken normal base pairing are introduced during amplification. Preferably, the ribonucleotides are inosine-triphosphate nucleotides which partly substitute guanine-triphosphate nucleotides normally present in the amplification reaction mixture. These ribonucleotides weaken normal base pairing and prevent the formation of secondary structures in the amplificate, thereby increasing the efficiency of amplification. Also, improved sensitivity results during detection of the amplified nucleic acid when the detection method comprises the hybridization of the amplified nucleic acid to a complementary sequence.

8 Claims, 1 Drawing Sheet

METHOD FOR NUCLEIC ACID AMPLIFICATION USING INOSINE TRIPHOSPHATES TO PARTIALLY REPLACE GUANOSINE TRIPHOSPHATES IN THE SYNTHESIS OF MULTIPLE RNA COPIES

This is a continuation of application Ser. No. 08/110,919 filed Aug. 24, 1993, now abandoned.

BACKGROUND OF THE INVENTION

The present invention relates to a method for the amplification of nucleic acid.

The amplification of specific nucleic acid segments is particularly useful for the generation of detectable amounts of certain kinds of nucleic acid. For example when the presence of nucleic acid characteristic for a specific disease state is to be indicated, this nucleic acid is generally present in biological samples in small amounts. To be able to detect these small amounts of nucleic acid either very sensitive detection methods would have to be used or very large amounts of sample material would have to be concentrated. With the present amplification techniques the small amounts of a specific segment of nucleic acid present in a biological sample can be amplified. This amplified nucleic acid can readily be detected by, for example, hybridizing it to a labelled complementary oligonucleotide. Of course the amplification of nucleic acid is also useful for the generation of larger amounts of nucleic acid used in recombinant DNA techniques and for cloning and sequencing purposes.

Known techniques for the amplification of specific nucleic acid segments are, for example, the polymerase chain reaction (PCR), as described in U.S. Pat. No. 4,683,195 and U.S. Pat. No. 4,683,202, and Nucleic Acid Sequence Based Amplification ("NASBA"), as described in European Patent application EP 0,329,822.

With PCR large amounts of deoxyribonucleic acid (DNA) are generated by treating a target DNA sequence with oligonucleotide primers such that a primer extension product is synthesized which is separated from the template using heat denaturation and in turn serves as a template, resulting in the amplification of the target DNA sequence. When RNA is to be amplified with PCR the RNA strand is first transcribed into a DNA strand with the aid of reverse transcriptase. Intermediates in the Polymerase Chain Reaction consist of DNA only.

With the aid of "NASBA" large amounts of single stranded RNA are generated from either single stranded RNA or DNA or double stranded DNA. When RNA is to be amplified with "NASBA" the ssRNA serves as a template for the synthesis of a first DNA strand by elongation of a first primer containing a RNA polymerase recognition site. This DNA strand in turn serves as the template for the synthesis of a second, complementary, DNA strand by elongation of a second primer, resulting in a double stranded active RNA-polymerase promoter site, and the second DNA strand serves as a template for the synthesis of large amounts of the first template, the ssRNA, with the aid of a RNA polymerase.

All amplification processes comprise the attachment of primers to templates and subsequent elongation of these primers by certain nucleic acid polymerases that may differ depending on the amplification technique employed.

A problem encountered with amplification of nucleic acid is that nucleic acid is capable of forming various secondary structures. Nucleic acid strands may comprise sequences that may result in the formation of, for example, hairpin loops. These secondary structures might hamper the attachment of a primer to a template and the subsequent elongation of the primer along the template. By interfering with the annealing or extension of the amplification primers these secondary structures lower the efficiency of the amplification.

By the incorporation during amplification of nucleotides that weaken normal base paring the formation of secondary structures, like the formation of internal loops, in the amplificate is prevented. With the incorporation of these structure destabilizing nucleotides secondary structures are destabilized and amplification will become more efficient.

The formation of secondary structures in nucleic acid is also known to be a problem with the sequencing of nucleic acid, because such structures, i.e. compressed regions, may result in anomalous migration patterns during gel electrophoresis. Substitution of inosine for guanosine in the nucleic acid fragments synthesized for the sequencing of RNA has been described by D. R. Mills et al., P.N.A.S., Vol.76, pp.2232–2235, May 1979. With the introduction of inosine in the nucleic acid fragments secondary structures are prevented and the resolution obtained in gel separations after sequencing of the nucleic acid is thereby improved.

The incorporation of a structure destabilizing base analog in DNA amplified with the Polymerase Chain Reaction has been described by Cetus Corporation in PCT application no. WO90/03443. The structure destabilizing nucleotide incorporated during PCR amplification in the method as claimed by Cetus is 7-deaza-2'-deoxyguanosine-5'-triphosphate ($c^7dGTP$).

The utilization of $c^7dGTP$ in PCR results in the incorporation of 7-deazaguanine into the amplified DNA product. This analog differs from normal guanine in that the N-7 of the guanine ring is replaced with a methine moiety which precludes Hoogsteen bond formation. For amplification processes with DNA intermediates the incorporation of $c^7dGTP$ increases amplification efficiency.

BRIEF DESCRIPTION OF THE INVENTION

The method of the present invention for the amplification of nucleic acid nucleotides is characterized in that ribonucleotides are introduced during amplification that weaken normal base pairing.

Certain RNA sequences are known to form very strong secondary structures that can hardly be disrupted. The ribonucleotides that weaken normal base pairing used with a method according to the present invention are incorporated in ribonucleic acid intermediates during amplification to make the ribonucleic acid less capable of forming secondary structures like hairpin loops that can hinder amplification.

Preferably, as a ribonucleotide that weakens with normal base pairing, inosine-triphosphate (ITP) is used. ITP is an analogue of guanine-triphosphate (GTP). Inosine differs from guanine, when incorporated in nucleic acid, in that it only forms two hydrogen bonds with cytosine whereas guanine forms three hydrogen bonds with cytosine. I-C base pairs therefore are relatively weak compared to normal G-C base pairs. Secondary structures, that are normally held together by the relatively strong G-C base pairs are therefore weakened by the incorporation of ITP or do not form at all. The ITP is incorporated in the ribonucleic acid during primer extension by a suitable nucleic acid polymerase. Since the nucleic acid strands thus obtained are less capable of forming secondary structures, they will serve as more efficient templates in subsequent amplification cycles.

DETAILED DESCRIPTION OF THE INVENTION

Figure 1:
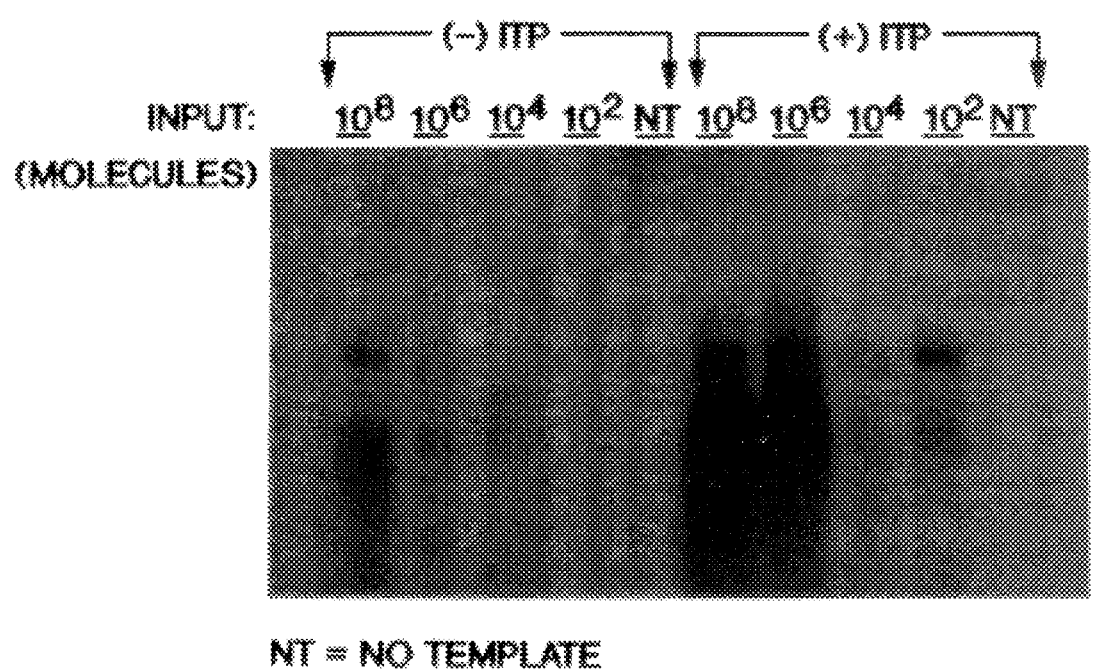
FIG. 1 is a gel showing the detection of nucleic acid amplified with and without ITP.
~~~

The method according to the invention is especially useful in amplification methods like "NASBA" that, unlike PCR, generate large amounts of RNA intermediates, starting from DNA as well as RNA.

The incorporation of inosine in DNA intermediates during amplification in PCR results in frequent mismatching of bases during primer extension, as is stated in the above mentioned PCT application of Cetus Corp. (WO 90/03443). Surprisingly with amplification techniques where RNA intermediates are generated good results are obtained and the error-rate of the amplification is certainly not higher than with conventional amplification, that is without the incorporation of ITP.

Especially when "NASBA" is used as the amplification technique, the incorporation of ITP during amplification might even result in a 10–100 times higher amplification factor. This means that, with the incorporation of ITP, 10–100 times more RNA will be produced from the originally amount of nucleic acid present in a biological sample than without the incorporation of ITP.

With the method according to the invention ITP can be added to the amplification mixture containing normal ribonucleotides like GTP, UTP, CTP and ATP.

Preferably the ITP added partly substitutes the GTP normally present. Good results are obtained when no more than 50% of the GTP present in a amplification reaction mixture is substituted with ITP.

When the ratio of ITP:GTP is too high the amplification is hampered. ITP has proven to be not as good as a substrate for the enzymes used with amplification, nucleic acid polymerases like the T7 polymerase used with NASBA, as normal GTP. The optimal ratio of ITP:GTP has been found to be approximately 1:3. In this way enough ITP will be incorporated in the amplified nucleic acid to interfere with the formation of rigid secondary structures while amplification is not yet hindered by the amount of ITP present in the amplification reaction mixture.

A kit for the amplification of nucleic acid, comprising a mixture of nucleotides characterized in that the mixture comprises ribonucleotides that weaken normal base pairing, is also part of the present invention. Such an amplification kit may further comprise suitable amplification primers for the specific nucleic acid to be amplified and other amplification reagents like the necessary enzymes.

The present invention also relates to a method for the detection of amplified nucleic acid where the nucleic acid is hybridized to a complementary detection probe and the nucleic acid to be detected was amplified with the method for the amplification of nucleic acid according to the invention. The incorporation of nucleotides that weaken normal base pairing during amplification results in both a more efficient amplification and a more sensitive detection. The hybridization of a complementary detection probe to the nucleic acid that is to be detected can also be affected by the presence of secondary structures in the amplified nucleic acid. The secondary structures can hinder the oligonucleotide in its binding to the amplified nucleic acid. The interference of secondary structures with the binding of a labelled oligonucleotide to the nucleic acid may reduce the sensitivity of the detection method. With the method for the detection of amplified nucleic acid according to the invention sensitivity is increased because the formation of secondary structures that interfere with the annealing of amplified nucleic acid and a complementary oligonucleotide is prevented. The advantage of the incorporation of the interfering nulceotides in the amplified nucleic acid therefore is twofold: not only the efficiency of the amplification is increased but also the sensitivity of detection methods, where nucleic acid is detected by hybridizing it to a detection probe, is markedly improved.

One common way in which the detection of amplified nucleic acid is often carried out is by subjecting the sample with amplified nucleic acid to gel electrophoresis, blotting the gel onto a filter and hybridizing the nucleic acid with a detection probe, where the detection probe is a labelled complementary oligonucleotide.

Nucleic acid to be detected that is amplified with the method according to the invention will be bound to the filter in a rather unwinded form because the formation of secondary structures is prevented by the incorporation of nucleotides that weaken normal base pairing. Because of the absence of secondary structures hybridization of a complementary sequence to the amplified nucleic acid present on a filter, or on any other solid phase, is improved.

Of course the detection method according to the invention is not limited to the above described embodiment. Any detection method involving hybridization of the amplified nucleic acid to a complementary sequence will benefit from the effects of the incorporation of nucleotides that weaken normal base pairing during amplification whereby the formation of secondary structures is prevented. The method according to the invention can equally well be applied to any other detection method where the amplified nucleic acid is hybridized to a complementary sequence. For example, the detection probe can also be a complementary oligonucleotide immobilized on a solid phase, like in a sandwich hybridization assay. In this case the amplified nucleic acid is bound to the solid phase by hybridizing to the complementary oligonucleotide immobilized on the solid phase and can be detected by hybridizing the immobilized amplified nucleic acid with a second, labelled, complementary oligonucleotide.

Furthermore the present invention relates to a test kit for the detection of amplified nucleic acid. Such a test kit may comprise suitable reagents for the amplification of the nucleic acid including a mixture of nucleotides comprising a certain amount of nucleotides that weaken normal base pairing, suitable amplification primers and enzymes (nucleic acid polymerases) and detection means like, for example, a solid phase with complementary oligonucleotides immobilized thereon to which the amplified nucleic acid can be bound and a second complementary labelled oligonucleotide.

Or, when the amplified nucleic acid is subjected to electrophoresis, suitable reagents, for detection of the nucleic acid after electrophoresis is completed, can be included in the test kit. Reagents for detection of the amplified nucleic acid after electrophoresis may comprise a labelled complementary oligonucleotide which may be hybridized to the amplified nucleic acid before or after electrophoresis. When the oligonucleotide is enzyme labelled the test kit may also comprise a suitable substrate for the enzyme label.

A possible embodiment of the present invention is given in Example 1. From this example, and FIG. 1 in which the results are depicted, it can be seen that incorporating ITP in the amplification procedure markedly improves the efficiency of the amplification procedure and results in a higher sensitivity during detection. The intensity of the signal obtained during detection is increased because of the improved binding of the labelled oligonucleotide to amplificate.

EXAMPLES

Example 1

Amplification of part of the HCV genome with NASBA and subsequent detection of amplified nucleic acid.

Vector pGem7z f(+) (Promega) contains an insertion in the sma I site (multiple cloning site), of 277 nt (UTR-region) of the HCV genome. The vector was called #14.

Transcription with T7-polymerase was performed according to the Promega protocol, thereby generating the (+) RNA strand.

In vitro generated (+)RNA was amplified according to the (standard) "NASBA"-sop.

ITP was added to the 2.5 µM "NASBA" buffer, the ITP:GTP ratio being 1:3.

The amplified nucleic acid was subjected to electrophoresis on a native gel system (3% nusive/1% agarose) and blotted onto zetaprobe membrane and hybridized to $^{32}$p labelled oligonucleotides complementary to an internal fragment of the amplificate.

Samples with different starting amounts of nucleic acid molecules (inputs varying from $10^2$ to $10^8$ molecules) were subjected to amplification.

The results obtained were compared to the results obtained when the same nucleic acid segment was amplified without the addition of ITP.

The results are given in FIG. 1. From this figure it can be seen that $10^2$ molecules input of nucleic acid amplified in the presence of ITP resulted already in a detectable band in the gel, whereas nucleic acid amplified in the absence of ITP only gave a detectable signal when amplification was started with $10^4$ molecules input.

We claim:

1. A method for the amplification of a target nucleic acid sequence into multiple copies of RNA, comprising:
   (a) providing a double stranded DNA template that includes a promoter recognized by a DNA-dependant RNA polymerase and the target sequence;
   (b) transcribing multiple copies of RNA from said double stranded DNA template using a DNA-dependent RNA polymerase and a mixture of ribonucleotide triphosphates including inosine-triphosphate, wherein the inosine-triphosphate nucleotides partially replace quanine-triphosphate nucleotides normally present in said mixture, and wherein the inosine-triphosphate is incorporated into said RNA, and wherein said RNA may act as a template for a subsequent generation of said double stranded DNA template;
   whereby said target nucleic acid is amplified.

2. The method according to claim 1, wherein the inosine-triphosphate nucleotides are substituted for no more than 50% of the guanine-triphosphate nucleotides.

3. The method according to claim 2, wherein the ratio of ITP:GTP is approximately 1:3.

4. The method of claim 1, wherein the promoter is a T7 promoter and the DNA-dependent RNA polymerase is T7 RNA polymerase.

5. The method according to claim 1, wherein the subsequent generation of said double stranded DNA from said RNA is accomplished by:
   hybridizing a first oligonucleotide primer to said RNA;
   synthesizing a DNA strand complementary to the RNA using an RNA-directed DNA polymerase to thereby produce an RNA-DNA hybrid intermediate;
   separating the DNA strand from the RNA-DNA hybrid intermediate using an enzyme having RNase H activity;
   hybridizing a second oligonucleotide primer, which includes said promoter sequence, to the DNA strand from the immediately preceding step;
   extending the second primer to thereby render the DNA double-stranded using a DNA-directed DNA polymerase.

6. The method of claim 5, further comprising reacting the double stranded DNA generated from said RNA with the DNA-dependent RNA polymerase and said mixture of ribonucleotides including inosine-triphosphate to thereby generate additional multiple copies of the RNA, which have ITP incorporated therein, whereby an amplification cycle ensues, which is continued until a desired level of amplification of the target sequence is reached.

7. A kit for the amplification of nucleic acid, comprising a mixture of the ribonucleotides, quanine-triphosphate, uridine-triphosphate, cytidine-triphosphate, adenine-triphosphate and inosine-triphosphate, wherein the ratio of inosine-triphosphate to guanine-triphosphate in said mixture is approximately 1:3.

8. A method for the detection of nucleic acid, comprising amplifying the nucleic acid in accordance with the method of claim 1, followed by hybridization of the generated RNA with a complementary labeled probe, and detecting the label of the hybridized probe, thereby detecting the nucleic acid.

* * * * *

UNITED STATES PATENT AND TRADEMARK OFFICE
CERTIFICATE OF CORRECTION

PATENT NO. : 5,654,142
DATED : August 5, 1997
INVENTOR(S) : Kievits et al.

It is certified that error appears in the above-indentified patent and that said Letters Patent is hereby corrected as shown below:

> Claim 1, column 5, last line, please delete "quanine" and replace with -- guanine --; and
> Claim 7, column 6, line 39, please delete "quanine" and replace with -- guanine --

Signed and Sealed this

Twenty-first Day of October 1997

Attest:

BRUCE LEHMAN

Attesting Officer

Commissioner of Patents and Trademarks